US010048142B2

(12) United States Patent
Kojima et al.

(10) Patent No.: US 10,048,142 B2
(45) Date of Patent: Aug. 14, 2018

(54) EVALUATION METHOD FOR BULK SILICON CARBIDE SINGLE CRYSTALS AND REFERENCE SILICON CARBIDE SINGLE CRYSTAL USED IN SAID METHOD

(71) Applicant: NIPPON STEEL & SUMIKIN MATERIALS CO., LTD., Tokyo (JP)

(72) Inventors: Kiyoshi Kojima, Osato-Gun (JP); Masashi Nakabayashi, Osato-Gun (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 15/314,731

(22) PCT Filed: May 30, 2014

(86) PCT No.: PCT/JP2014/064475
§ 371 (c)(1),
(2) Date: Nov. 29, 2016

(87) PCT Pub. No.: WO2015/181971
PCT Pub. Date: Dec. 3, 2015

(65) Prior Publication Data
US 2017/0199092 A1 Jul. 13, 2017

(51) Int. Cl.
*G01L 1/24* (2006.01)
*G01L 5/00* (2006.01)
*G01N 21/65* (2006.01)

(52) U.S. Cl.
CPC ............. *G01L 1/24* (2013.01); *G01L 5/0047* (2013.01); *G01N 21/65* (2013.01)

(58) Field of Classification Search
CPC .................................. G01L 1/24; G01N 21/65
See application file for complete search history.

(56) References Cited

U.S. PATENT DOCUMENTS 7,767,022 B1 * 8/2010 Gupta ................... C30B 23/00
117/105
2003/0010275 A1 * 1/2003 Radojevic ............... C30B 31/22
117/2
(Continued)

FOREIGN PATENT DOCUMENTS

JP   3-18744 A   1/1991
JP   6-26945 A   2/1994
(Continued)

OTHER PUBLICATIONS

English translation of Aigo et al. (JP2008103650).*
(Continued)

*Primary Examiner* — Dominic J Bologna
(74) *Attorney, Agent, or Firm* — Birch, Stewart, Kolasch & Birch, LLP

(57) ABSTRACT

Provided are a method by which the degrees of the strains of lattices in a plurality of bulk SiC single crystals can be relatively evaluated, and a reference SiC single crystal to be used in the method. Specifically provided are an evaluation method for bulk-shaped silicon carbide single crystals, including: measuring a Raman shift $R_{ref}$ of a reference silicon carbide single crystal to be used as a standard; measuring respective Raman shifts $R_n$ of a plurality of bulk-shaped silicon carbide single crystals serving as objects to be evaluated; determining differences between each of the Raman shifts $R_n$ and the Raman shift $R_{ref}$; and relatively comparing the differences, to thereby relatively evaluate magnitudes of strains of lattices in the plurality of bulk-shaped silicon carbide single crystals serving as objects to be evaluated, and a reference silicon carbide single crystal to be used in the method, having a size of 5 mm square or more and 50 mm square or less and a thickness of 100 μm or more and 2,000 μm or less, having a surface roughness Ra of 1 nm (Continued)

or less, and having a micropipe density of $1.0/cm^2$ or less and a dislocation density of $5 \times 10^3/cm^2$ or less.

19 Claims, 3 Drawing Sheets

(56) References Cited

U.S. PATENT DOCUMENTS

| | | | |
|---|---|---|---|
| 2003/0146748 A1* | 8/2003 | Duncan | G01R 15/245 |
| | | | 324/244.1 |
| 2007/0059501 A1* | 3/2007 | Kaneko | C23C 8/02 |
| | | | 428/209 |
| 2008/0084552 A1 | 4/2008 | Naka et al. | |
| 2008/0086276 A1 | 4/2008 | Naka et al. | |
| 2009/0170298 A1* | 7/2009 | Brailove | B28D 1/221 |
| | | | 438/532 |
| 2012/0280355 A1* | 11/2012 | Akiyama | H01L 21/76254 |
| | | | 257/507 |
| 2013/0032822 A1* | 2/2013 | Ishibashi | H01L 21/02002 |
| | | | 257/77 |
| 2013/0056752 A1* | 3/2013 | Fujiwara | H01L 21/046 |
| | | | 257/77 |
| 2014/0097444 A1* | 4/2014 | Fang | H01L 33/025 |
| | | | 257/76 |
| 2014/0363607 A1* | 12/2014 | Sato | C30B 29/36 |
| | | | 428/64.1 |
| 2015/0085348 A1* | 3/2015 | Mildren | H01S 3/30 |
| | | | 359/327 |

FOREIGN PATENT DOCUMENTS

| | | | |
|---|---|---|---|
| JP | 2001-122692 A | 5/2001 | |
| JP | 2004-131328 A | 4/2004 | |
| JP | 2005-322944 A | 11/2005 | |
| JP | 2006-290705 A | 10/2006 | |
| JP | 2008-103650 A | 5/2008 | |
| JP | 2001-247906 A | 12/2011 | |
| JP | 2013-53049 A | 3/2013 | |
| JP | 2014-28757 A | 2/2014 | |
| WO | WO 2013/021902 A1 | 2/2013 | |
| WO | WO 2013031856 A1 * | 3/2013 | C30B 29/36 |

OTHER PUBLICATIONS

English translation of Izumi et al. (JP 2001122692).*
Mermoux et al. "Raman imaging analysis of SiC wafers" Materials Science Forum vols. 433-436, pp. 353-356.*
International Search Report, issued in PCT/JP2014/064475, dated Sep. 2, 2014.
Ito et al., "Stress Analysis in Micro Areas of LSIs Using Raman Microprobe", R&D Review of Toyota CRDL, Dec. 1994, vol. 29, No. 4, pp. 43-51, total 10 pages.
English translation of the International Preliminary Report of Patentability, (Forms PCT/IB/388 and PCT/IPEA/409), dated Dec. 1, 2016, for the International Application No. PCT/JP2014/064475.
Extended European Search Report, dated Dec. 22, 2017, for corresponding European Application No. 14893482.1.

* cited by examiner

EVALUATION METHOD FOR BULK SILICON CARBIDE SINGLE CRYSTALS AND REFERENCE SILICON CARBIDE SINGLE CRYSTAL USED IN SAID METHOD

TECHNICAL FIELD

The present invention relates to an evaluation method for bulk-shaped silicon carbide single crystals, and to a reference silicon carbide single crystal to be used in the method. More specifically, the present invention relates to an evaluation method for bulk-shaped silicon carbide single crystals by which magnitudes of strains of lattices of a plurality of bulk-shaped silicon carbide single crystals serving as objects to be evaluated can be relatively evaluated through use of Raman spectroscopy, and to a reference silicon carbide single crystal to be used in the method.

BACKGROUND ART

Silicon carbide (SiC) is a wide-bandgap semiconductor having a wide forbidden bandgap of from 2.2 eV to 3.3 eV. Because of its excellent physical and chemical characteristics, research and development of SiC as an environment-resistant semiconductor material have been performed. Particularly in recent years, SiC has been attracting attention as a material for, for example, a device for short-wavelength light ranging from blue to ultraviolet, a high-frequency electronic device, or a high-voltage and high-output electronic device, such as a power semiconductor. Research and development have been actively performed on production of a device (semiconductor device) based on SiC.

In promoting practical use of the SiC device, it is indispensable to produce a large-diameter SiC single crystal. In many of such cases, a method involving growing a bulk SiC single crystal by a sublimation recrystallization method, which is called a modified Lely method, is adopted. That is, crystal powder of SiC is placed in a crucible, a seed crystal formed of a SiC single crystal is attached onto a lid of the crucible, and the SiC crystal powder is sublimated, to thereby grow a SiC single crystal on the seed crystal. Thus, an ingot SiC single crystal having a substantially cylindrical shape is obtained. After that, the ingot SiC single crystal is generally cut into a thin plate shape having a thickness of from about 300 µm to about 600 µm using a multi-wire saw or the like and is subjected to any of various kinds of polishing treatment to produce a SiC single crystal substrate.

In the case of the sublimation recrystallization method, a crystal is generally grown under a state in which a temperature gradient is formed so that the temperature is lower on a seed crystal side as compared to a SiC crystal powder side serving as a raw material for a grown crystal. In this case, the inside of a growth space is controlled to form an isotherm having an appropriate convex shape toward a growth direction, so that a good-quality SiC single crystal ingot may be obtained. However, such temperature difference in the growth space also causes a thermal stress to remain in the SiC single crystal thus grown. Such thermal stress varies for each ingot obtained, and hence may generate a crack (cracking) in the ingot as an accidental trouble during cutting with a multi-wire saw, for example.

In addition, in production of the SiC single crystal substrate, a processing strain is formed by cutting of a thin plate-like SiC single crystal out of the SiC single crystal ingot and polishing thereof. The processing strain appears as warpage of the SiC single crystal substrate, and such warpage may pose a significant problem, such as causing defocus in an exposure process during device production. Accordingly, in ordinary cases, the processing strain is removed by diamond polishing, chemical mechanical polishing (CMP), or the like. However, if the processing strain remains or the SiC single crystal substrate has a thermal stress as an internal stress, when an epitaxial film is formed for use in a device production application, the resultant SiC single crystal epitaxial wafer may warp.

As a measure against those problems, there is known a method involving annealing the SiC single crystal ingot or the SiC single crystal substrate at a high temperature around 2,000° C., to thereby remove the thermal stress or the processing strain remaining in the silicon carbide single crystal (see, for example, Patent Literatures 1 and 2). However, no method of efficiently evaluating the thermal stress or the processing strain in the SiC single crystal has been known heretofore.

For example, through precise measurement of lattice constants using an X-ray, it is technically possible to evaluate a strain of a lattice of a single crystal. However, the measurement is not suited for industrial utilization because of, for example, the following reasons: the measurement requires expensive equipment and high skills for its implementation, and the measurement requires a long period of time.

Meanwhile, for a gallium nitride-based semiconductor light-emitting device having a laminated structure in which an n-type GaN layer, a light-emitting layer, and a p-type GaN layer are arranged on a sapphire substrate, there is a disclosure of a method of evaluating an average lattice strain amount of the GaN layer over all the layers of the laminated structure through use of Raman spectroscopy (see Patent Literature 3). In this method, a Raman shift is measured in such a manner that excitation light reaches all the layers in the laminated structure, and the measured value is converted to an a-axis lattice strain amount of the GaN layer on the basis of a known value.

However, in the case of Patent Literature 3, evaluation based on the Raman shift can be performed probably because a lattice strain is generated due to differences in lattice constants between the sapphire substrate and GaN, and also due to a tensile stress resulting from differences in lattice constants among the layers including the n-type GaN layer, the light-emitting layer, and the p-type GaN layer. That is, a difference (Raman shift) between a frequency of Raman-scattered light and a frequency of incident light is very slight in the first place, and hence a lattice strain of a SiC single crystal alone is difficult to evaluate. In addition to Patent Literature 3, there is a report of an example in which fine LSI obtained by bonding a dissimilar metal onto a Si substrate is measured for stress distribution in the vicinity of a titanium silicide pattern in the fine LSI, and in the vicinity of an element isolation film through use of micro-Raman spectroscopy (see Non Patent Literature 1). However, it is disclosed that a large stress of from 150 MPa up to 350 MPa acts on the Si substrate in the vicinity of the titanium silicide pattern. Accordingly, the measurement is performed under a state in which a large lattice strain is induced after all.

Besides, the Raman shift is liable to be subjected to influences of fluctuation in wavelength of laser light of a Raman spectroscope to be used for measurement and a thermal strain of the measuring instrument, and hence reproducibility of its measurement is not sufficient. Accordingly, even when it is in principle or in investigatory terms possible to measure the Raman shift, the measurement is not suited for evaluating a lattice strain of a single crystal alone in an industrial production application.

CITATION LIST

Patent Literature

[PTL 1] JP 2004-131328 A
[PTL 2] JP 2006-290705 A
[PTL 3] JP 2005-322944 A

Non Patent Literature

[NPL 1] Tadashi Ito, Hirozumi Azuma, and Shoji Noda: "Stress Analysis in Micro Areas of LSIs Using Raman Microprobe," "R&D Review of Toyota CRDL," Vol. 29, No. 4 (1994.12) p. 43-p. 51

SUMMARY OF INVENTION

Technical Problem

In view of the foregoing, the inventors of the present invention have made extensive investigations on a method of evaluating the degree of the strain of a lattice in a bulk-shaped SiC single crystal, such as a SiC single crystal ingot or a SiC single crystal substrate, and as a result, have found that the magnitudes of the strains of lattices in a plurality of bulk-shaped silicon carbide single crystals serving as objects to be evaluated can be relatively evaluated by: measuring the Raman shift of a reference SiC single crystal to be used as a standard; measuring the respective Raman shifts of the plurality of bulk-shaped SiC single crystals serving as objects to be evaluated; determining differences between each of the Raman shifts and the Raman shift of the reference SiC single crystal; and relatively comparing the differences. Thus, the inventors have completed the present invention.

Therefore, an object of the present invention is to provide a method by which the degrees of the strains of the lattices of a plurality of bulk SiC single crystals serving as objects to be evaluated can be relatively evaluated.

In addition, another object of the present invention is to provide a reference SiC single crystal to be used in a method of relatively evaluating the degrees of the strains of the lattices of bulk SiC single crystals.

Solution to Problem

That is, according to one embodiment of the present invention, there is provided an evaluation method for bulk-shaped silicon carbide single crystals, including: measuring a Raman shift $R_{ref}$ of a reference silicon carbide single crystal to be used as a standard; measuring respective Raman shifts $R_n$ of a plurality of bulk-shaped silicon carbide single crystals serving as objects to be evaluated; determining differences between each of the Raman shifts $R_n$ and the Raman shift $R_{ref}$; and relatively comparing the differences, to thereby relatively evaluate magnitudes of strains of lattices in the plurality of bulk-shaped silicon carbide single crystals serving as objects to be evaluated.

According to another embodiment of the present invention, there is provided a reference silicon carbide single crystal to be used in the above-mentioned method, for use in evaluation of bulk-shaped silicon carbide single crystals, the reference silicon carbide single crystal having a size of 5 mm square or more and 50 mm square or less and a thickness of 100 μm or more and 2,000 μm or less, having a surface roughness Ra of 1 nm or less, and having a micropipe density of 1.0/cm² or less and a dislocation density of 5×10³/cm² or less.

In general, when an attempt is made to measure the lattice strain of a bulk-shaped SiC single crystal (sometimes referred to simply as "bulk SiC single crystal") by Raman spectroscopy, for example, a Raman shift resulting from an internal stress is very slight because of, for example, a strong covalent bond of the SiC single crystal. This is also associated with the fact that SiC has a Young's modulus of from about 479.3 GPa to about 521.6 GPa (The Single Crystal Elastic Constants of Hexagonal SiC to 1000° C. Nov. 10, 1987, Z. Li & R. C. Bradt, Int J High Technology Ceramics 4 (1988) p. 1-10), which is from about 2 to about 3 times as large as that of Si, which is from about 130 GPa to about 180 GPa. That is, on the basis of the relational expression "(strain)=(stress)/(Young's modulus)," the strain amount of SiC having a large Young's modulus is small even when a large stress acts thereon. Accordingly, the accuracy of a Raman spectroscope is insufficient for direct measurement of the strain amount (i.e., lattice spacing).

Besides, a Raman shift is liable to be subjected to the influences of fluctuation in wavelength of laser light of the Raman spectroscope to be used for measurement and the thermal strain of the measuring instrument, and hence the measurement of the lattice strain of a SiC single crystal alone is poor in reproducibility. In FIG. 1, results of measurement of a Raman shift (cm⁻¹) once daily for the same sample using a bulk SiC single crystal piece having a thickness of about 350 μm are shown. It is apparent from the results that the Raman shift has varying values depending on the state of the apparatus, a measurement environment, and the like. In particular, a thermal stress and a strain amount in the growth of a SiC single crystal by a sublimation recrystallization method are generally estimated to be from about 10 MPa to about 100 MPa and from about 1/10,000 to about 1/1,000,000, respectively, whereas the influences of fluctuation in wavelength of the laser light and the thermal strain of the measuring instrument as described above are considered to be comparable to or higher than those values. Accordingly, even when measurement is performed for the same sample, the value changes in the order of from 1/1,000 to 1/10,000, and hence sufficient reproducibility of measurement cannot be attained.

In view of the foregoing, in the present invention, the Raman shift $R_{ref}$ of the reference SiC single crystal to be used as a standard is measured, and the respective Raman shifts $R_n$ of the plurality of bulk-shaped silicon carbide single crystals serving as objects to be evaluated are measured (n≥1). In addition, differences between each of the Raman shifts $R_n$ and the Raman shift $R_{ref}$ such as $(R_1-R_{ref})$, $(R_2-R_{ref})$, ..., $(R_n-R_{ref})$ (of course, $(R_{ref}-R_1)$ etc. are also permitted), are determined, and the differences are relatively compared. Thus, the plurality of bulk SiC single crystals serving as objects to be evaluated can be relatively evaluated, for example, as follows: a SiC single crystal ingot of Sample No. 1 (n=1) produced by a sublimation recrystallization method has a small strain of a lattice as compared to a SiC single crystal ingot of Sample No. 2 (n=2) also produced by the sublimation recrystallization method. Consequently, even in Raman spectroscopy, which is liable to be subjected to the influences of the state of the apparatus, the measurement environment, and the like, the problem with reproducibility does not arise, and the degrees of the strains of the lattices can be compared simply and accurately for the bulk SiC single crystals alone. In addition, even when not all of the bulk SiC single crystals serving as objects to be evaluated can be measured for their Raman shifts $R_n$ at the same timing, as long as the Raman shift of each of the bulk SiC single crystals serving as objects to be evaluated is measured together with that of the reference SiC single crystal, the degrees of the strains of the bulk SiC single crystals can be relatively evaluated by comparison based on the differences between the Raman shifts for the measurement of the Raman shifts of the bulk SiC single crystals serving as objects to be evaluated and the reference SiC single crystal performed at different timing.

In the present invention, in the relative evaluation of the bulk SiC single crystals, the same reference SiC single crystal is used. That is, the magnitudes of the strains of the lattices in the bulk SiC single crystals serving as objects to be evaluated are relatively evaluated by using the Raman shift $R_{ref}$ of the reference SiC single crystal as a standard, and determining the differences between each of the respective Raman shifts $R_n$ of the bulk SiC single crystals serving as objects to be evaluated and the Raman shift $R_{ref}$ and hence any SiC single crystal may be used as the reference SiC single crystal to be used as a standard. The polytype of the reference SiC single crystal is preferably set to be the same as that of each of the bulk SiC single crystals serving as objects to be evaluated. It is more preferred from the viewpoint of further facilitating relative comparison by achieving larger differences between the Raman shifts $R_n$ and the Raman shift $R_{ref}$ that the strain of the lattice of the reference SiC single crystal be suppressed to the extent possible.

In general, a smaller crystal has a smaller strain and provides a more ideal crystal having higher perfection. Accordingly, when a sublimation recrystallization method is employed in the production of the reference SiC single crystal, it is recommended that a SiC single crystal having a small diameter be grown as compared to the case of being grown in a device production application. In addition, as the thickness is reduced, the strain is relaxed and the crystal lattice approaches a more natural one. For this reason, it is recommended that the thickness of the reference SiC single crystal be set to 2,000 µm or less. In this case, when the thickness is 1 µm or more, no problem arises in measurement in terms of the depth of focus in the measurement of a Raman shift. However, when the viewpoint of handleability for, for example, the prevention of cracking is taken into consideration, it is desired that the thickness of the reference SiC single crystal be 100 µm or more and 2,000 µm or less. A size of about 5 mm×5 mm (5 mm square) is sufficient for the measurement of a Raman shift itself, but in consideration of handleability and the like, it is recommended that the size of the reference SiC single crystal be 5 mm square or more and 50 mm square or less, preferably 10 mm square or more and 50 mm square or less. In an ingot of a SiC single crystal produced by a sublimation recrystallization method, a compressive stress is liable to be present in the central portion of a cross-section, whereas a tensile stress is liable to be present in the peripheral portion (edge portion) thereof. Accordingly, when the reference SiC single crystal is to be obtained from such SiC single crystal ingot, it is recommended that the reference SiC single crystal be taken out of a region having a comparatively neutral stress and a small strain, and it is suitable that, for example, as illustrated in FIG. 2, a doughnut-shaped region ranging from R/3 to 2R/3 excluding the central portion and the edge portion from a cross-section of a SiC single crystal ingot having a diameter of 100 mm or more be used (R represents the radius of the ingot, and FIG. 2 is an example of a situation in which a reference SiC single crystal having a size of 10 mm square is taken out).

In addition, it is recommended that the reference SiC single crystal be a high-quality one with less dislocations and less defects from the viewpoint of, for example, the prevention of an external disturbance in the measurement of its Raman shift. It is preferred that the reference SiC single crystal have a micropipe density of $1/cm^2$ or less (more preferably $0/cm^2$) and a dislocation density of $5,000/cm^2$ or less. In addition, it is suitable that the reference SiC single crystal be a 4H single-polytype SiC single crystal and have a nitrogen concentration of from $5\times10^{18}$ atoms/$cm^3$ to $5\times10^{19}$ atoms/$cm^3$. When the nitrogen concentration is lower than the range, a polytype of 6H or the like is liable to be generated in addition to 4H. On the other hand, when the nitrogen concentration is higher than the range, a 3C type or a lamination defect is liable to be generated.

Further, it is desired that a processing strain in the production of the reference SiC single crystal be removed by diamond polishing, chemical mechanical polishing (CMP), or the like. In this case, it is recommended that both surfaces of the reference SiC single crystal, i.e., its Si surface and C surface be set to the same level of surface roughness. Specifically, it is recommended that the reference SiC single crystal have a surface roughness Ra of 1 nm or less, preferably a surface roughness Ra of 0.2 nm or less, so as to remove therefrom the influence of a strain due to a strain difference between its front and back sides. In particular, it is recommended that both surfaces of the reference SiC single crystal, i.e., its Si surface and C surface be treated by chemical mechanical polishing. With this, the intensity of Raman scattering can be secured without the attenuation of scattered light. The surface roughness Ra refers to an arithmetic average roughness specified in JIS B0601 (1994). In addition, when the reference SiC single crystal is, for example, placed in a tray made of plastic, its handling is facilitated and contamination by sebum of a hand can be prevented.

In addition, as described above, through use of the reference SiC single crystal having as good crystallinity as possible and as high perfection of a crystal lattice as possible, quantitativity in the evaluation method according to the present invention can be secured. To identify the perfection of the crystal lattice, an evaluation technique called an X-ray rocking curve may be used. The X-ray rocking curve is a method of evaluating crystallinity and lattice strain by allowing an X-ray that has been made monochromatic and has good parallelism to enter a single crystal substrate or the like, and comparing a measured diffraction intensity curve to a theoretically calculated diffraction intensity curve. In the case of a SiC single crystal, specifically, the plane straightness of its C surface is measured from angular analysis of a diffraction line based on the projection of an X-ray on the C surface, and the perfection of the crystal is evaluated. In this case, when the half width of the X-ray rocking curve is 15 sec (arcsec) or less, the crystal may be regarded as being close to a substantially perfect crystal in practical use. This means that lattices are regularly arranged with an accuracy of about four thousandths of a degree or less as it follows from 1°=3,600 sec (arcsec) that 15 sec=0.004°.

In addition, for example, when the objects to be evaluated are bulk SiC single crystals each having a polytype of 4H, which are useful as materials for power devices, it is preferred that the reference SiC single crystal to be used have a polytype of 4H and have lattice constants within the following <Ranges 1>, more preferably lattice constants within the following <Ranges 2>. The lattice constants of a SiC single crystal slightly change depending on the concentration of a doping element, such as N, as well as on a thermal strain at the time of crystal growth and temperature history in a cooling process. However, with such lattice constants, the SiC single crystal is considered to be in a substantially typical natural form.

<Ranges 1>
10.058≤c≤10.060 (Å)
3.070≤a≤3.072 (Å)
2.659≤m≤2.661 (Å)

<Ranges 2>
10.05903≤c≤10.05916 (Å)
3.071114≤a≤3.071497 (Å)
2.659663≤m≤2.659994 (Å)

Meanwhile, the bulk SiC single crystals to be evaluated may encompass, for example, various kinds, ranging from SiC single crystal ingots produced by a sublimation recrystallization method, to thin plate-like SiC single crystals cut out of SiC single crystal ingots to SiC single crystal substrates that have undergone any of various kinds of polishing. In particular, in such a case that it is expected that the strain of the lattice of a bulk SiC single crystal exhibits some influence during processing treatment, the evaluation method of the present invention can be suitably utilized. That is, during wire processing involving slicing a SiC single crystal ingot into a thin plate shape, or during processing of the side surface of the ingot involving grinding the outer periphery of the SiC single crystal ingot into a cylindrical shape, in order to predict the generation of a crack or the like, the SiC single crystal ingot may be evaluated by the method of the present invention. In addition, in the growth of an epitaxial film on a SiC single crystal substrate, in order to predict the generation of warpage or the like, the SiC single crystal substrate may be evaluated by the method of the present invention. However, the bulk SiC single crystals to be evaluated are not limited to those described above. In addition, the lower limit of the thickness of each of the bulk SiC single crystals is not particularly limited, but when the depth of penetration of a laser beam and the attenuation of scattered light are taken into consideration, it is recommended that SiC single crystals each having a thickness of 10 μm or more be adopted. The method of the present invention is suited for evaluating the strain of the lattice of a bulk SiC single crystal alone, but its utilization for evaluation under a state in which another member, crystal, or the like is laminated on the bulk SiC single crystal is not excluded.

In addition, in the measurement of a Raman shift, when the depth of focus of an incident laser beam is set to a depth of from about 1 μm to about 100 μm, the strain of a lattice by the internal stress of a bulk SiC single crystal, such as a thermal stress due to a thermal gradient in sublimation recrystallization, can be evaluated. When the depth of focus is shallower than that range, the strain of the lattice resulting from a processing strain of slicing or the like is evaluated, and the depth of focus of the incident laser beam only needs to be appropriately selected as required. In addition, when the thickness of each of the bulk SiC single crystals serving as objects to be evaluated is 500 μm or less, through the measurement of the Raman shifts under a state in which each of the bulk SiC single crystals is attached onto a supporting pedestal having a horizontal mounting surface, the internal stresses of the SiC single crystals themselves, excluding the influence of stress release by warpage, can be evaluated. When the depth of focus of the incident laser beam is deeper than 100 μm, there is a risk in that Raman-scattered light is absorbed by SiC to prevent the intensity of Raman scattering from being sufficiently obtained.

In addition, with regard to a site at which a Raman shift is measured, it suffices to select a common place in each of the bulk SiC single crystals serving as objects to be evaluated in accordance with purposes, such as: the center or peripheral edge portion of a SiC single crystal substrate; or in a SiC single crystal ingot, the center of a growth surface or a surface on a seed crystal side, an edge portion of any such surface, or the same site of an ingot side surface.

In the evaluation method of the present invention, the Raman shift $R_n$ is measured at at least one site of each of the bulk SiC single crystals serving as objects to be evaluated, the differences between the Raman shifts $R_n$ and the Raman shift $R_{ref}$ of the reference SiC single crystal are determined, and the differences are relatively compared, to thereby relatively evaluate the magnitudes of the strains of the lattices in the plurality of bulk SiC single crystals serving as objects to be evaluated. That is, the measurement of their strains is not required to be performed between all lattices of the bulk SiC single crystals serving as objects to be evaluated, and on the basis of the strains of the lattices at the depth of focus of the incident laser beam at the measurement site, whether or not each of the bulk SiC single crystals serving as objects to be evaluated has a large strain as compared to others is determined. Accordingly, for example, for a SiC single crystal ingot determined to have a large degree of the strain of the lattice as compared to others, the generation of a crack can be prevented by, for example, making the conditions of wire processing or the like comparatively mild, or by performing treatment for removing an internal stress through annealing in advance. Of course, a bulk SiC single crystal subjected to annealing treatment or the like may be evaluated again by the method of the present invention.

Advantageous Effects of Invention

According to the present invention, the degrees of the strains of the lattices of a plurality of bulk SiC single crystals serving as objects to be evaluated can be relatively evaluated. Accordingly, for example, the generation of a crack during processing of a SiC single crystal ingot can be prevented, and the generation of warpage can be prevented during the growth of an epitaxial film on a SiC single crystal substrate.

DESCRIPTION OF EMBODIMENTS

Now, the present invention is specifically described by way of Examples. However, the present invention is not limited to the contents of Examples.

EXAMPLES

Example 1

Figure 1:
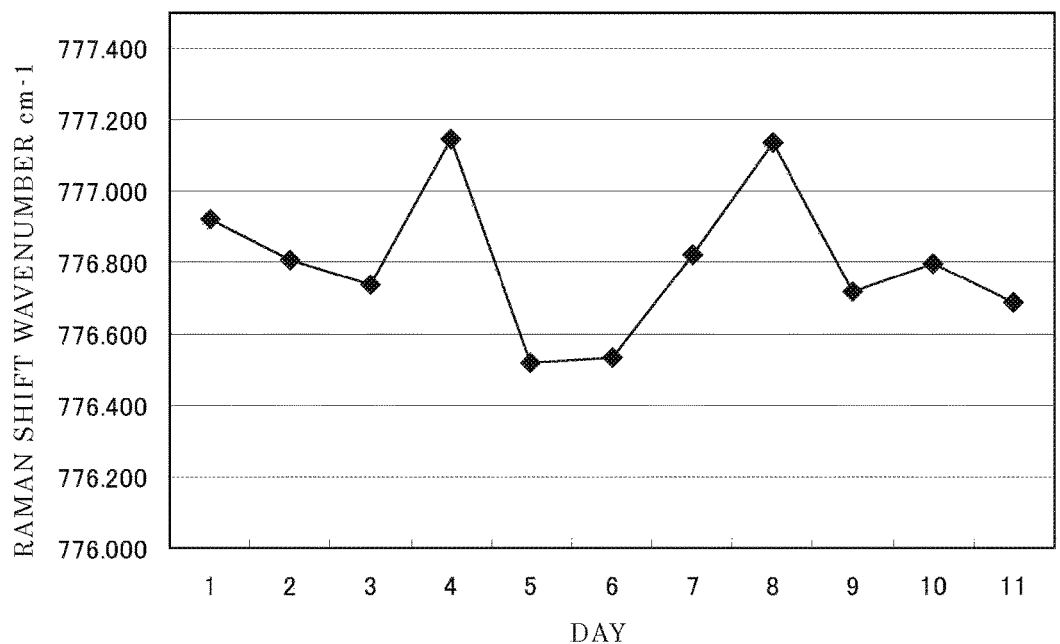
FIG. 1 is a graph for showing results of measurement of the Raman shift of a SiC single crystal piece on different measurement dates.
Figure 2:
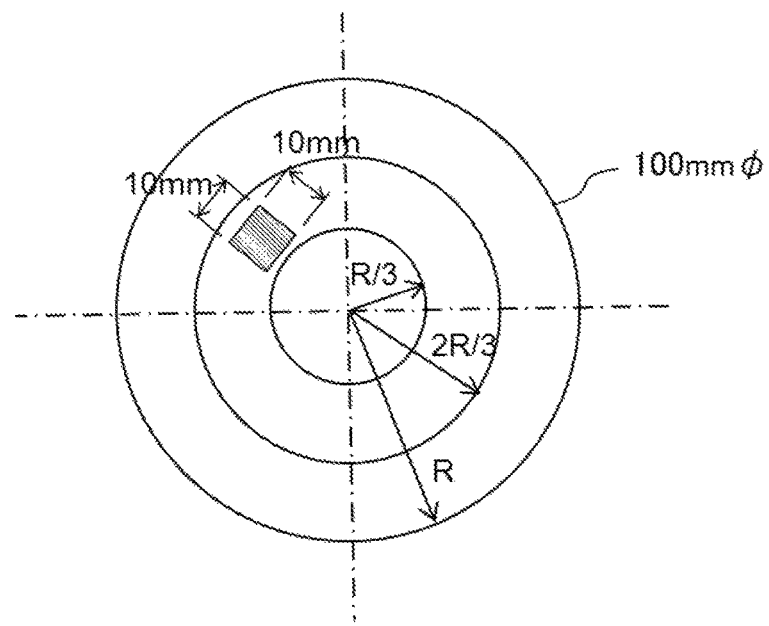
FIG. 2 is a schematic explanatory diagram for illustrating a situation in which a reference SiC single crystal is taken out of a SiC single crystal ingot.
Figure 3A:
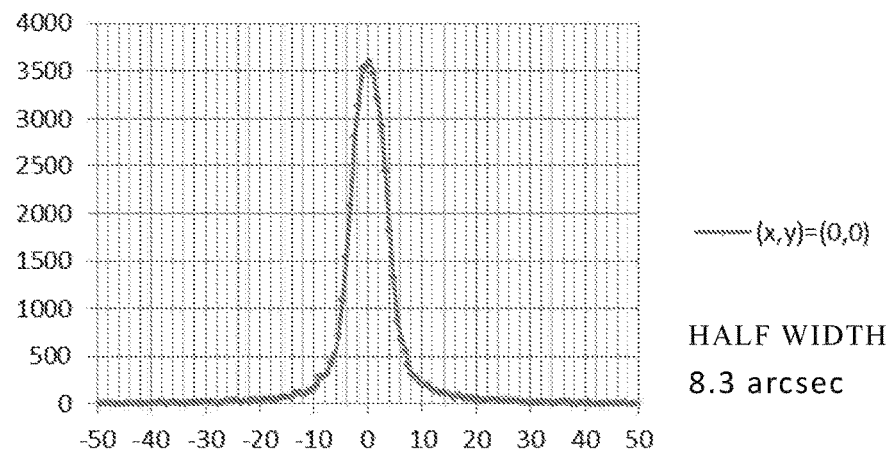
FIG. 3(a) is a graph for showing an X-ray rocking curve of a reference SiC single crystal used in Example 1.

First, a 2-inch (diameter: 55 mm) 4H-type SiC single crystal ingot produced by a sublimation recrystallization method was subjected to outer periphery grinding. After that, the resultant was cut using a multi-wire saw to a thickness of 0.5 mm, polished by diamond polishing to a thickness of 0.36 mm, and finally subjected to chemical mechanical polishing (CMP) to be finished into a substrate. The surface roughness was set to 0.1 nm in terms of Ra. Then, a square-shaped chip of 10 mm square was cut out of the central portion of the substrate to provide a reference SiC single crystal having a thickness of 0.35 mm and a size of 10 mm×10 mm. The SiC single crystal ingot of which the reference SiC single crystal was taken out had a nitrogen concentration of from $6\times10^{18}$ atoms/$cm^3$ to $9\times10^{18}$ atoms/$cm^3$. Etch pits were observed through molten alkali etching in the vicinity of the reference SiC single crystal taken out, and the reference SiC single crystal was found to have a dislocation density of $4.8\times10^3/cm^2$ and micropipes at $0.6/cm^2$. Further, a wafer cut out of the SiC single crystal ingot of which the reference SiC single crystal was taken out was measured for its X-ray rocking curve and, as shown in FIG. 3(a), was found to have a half width of 8.3 arcsec.

The reference SiC single crystal produced as described above was subjected to X-ray diffraction (XRD) measurement to determine its lattice constants, which were as follows: c=10.05913, a=3.071234, m=2.659678. In this connection, a 4H-type SiC single crystal has a hexagonal crystal structure, and its crystal planes are defined by a c-plane, an a-plane, and an m-plane. In view of this, in the XRD measurement, an X-ray is allowed to enter each of a reflection surface including a c-axis component in its normal line, a reflection surface including an a-axis component in its normal line, and a reflection surface including an m-axis component in its normal line, diffraction peaks thereof are analyzed, and lattice plane spacings are calculated from angles satisfying Bragg conditions. That is, a lattice plane spacing between c-planes is obtained from the Bragg condition for the c-plane. Similarly, a lattice plane spacing between a-planes is obtained from the Bragg condition for the a-plane, and a lattice plane spacing between m-planes is obtained from the Bragg condition for the m-plane.

The XRD measurement was performed using a high-accuracy X-ray diffraction apparatus having an accuracy of 0.00001 Å under the following conditions. An X-ray source is a rotary anticathode (copper target) and has a rated output of 18 kW. The entrance and detection of an X-ray were performed in parallel to the <11-20> direction of the reference SiC single crystal. Measurement sites were set to the following two sites: the center of the reference SiC single crystal and a position 2 mm away from its edge. In addition, precise X-ray diffraction was performed on three reflection surfaces, i.e., {00012}, {11-28}, and {1-1010}, lattice strains of the three principal planes of SiC, i.e., {0001}, {11-20}, and {1-100} were calculated, and the lattice constants a, c, and m were determined. The measurement took about 6 hr. In addition, when the Raman shift of the reference SiC single crystal was measured by a measurement method to be described later, its peak wavenumber was 776.0 $cm^{-1}$, but the Raman shift changed depending on the measurement time slot and the measurement date, and varied approximately between 775.8 $cm^{-1}$ and 776.2 $cm^{-1}$. In the foregoing, {00012} represents {0, 0, 0, 12}, and {1-1010} represents {1, -1, 0, 10}.

Next, as objects to be evaluated, four kinds of SiC single crystal ingots A to D produced by a sublimation recrystallization method were prepared. The ingots A to D each have a polytype of 4H, and have diameters, heights, and nitrogen concentrations shown in Table 1 below. For the evaluation of the strain of the lattice of each of the ingots A to D, a Raman shift was measured using Raman spectroscopy as described below. First, on the first day of measurement, a Raman shift $R_{ref}$ was measured at the center of the reference SiC single crystal obtained as described above, and a Raman shift $R_A$ was measured at the center in the C surface of the ingot A to determine a difference ($R_A-R_{ref}$) between the Raman shifts. In addition, on the second day of measurement, the Raman shift $R_{ref}$ was measured again at the center of the reference SiC single crystal, and a Raman shift $R_B$ was measured at the center in the C surface of the ingot B to determine a difference ($R_B-R_{ref}$) between the Raman shifts. In this way, Raman shifts were similarly measured for the ingot C (third day of measurement) and the ingot D (fourth day of measurement) to determine differences between their Raman shifts and the Raman shift $R_{ref}$ of the reference SiC single crystal.

Figure 4:
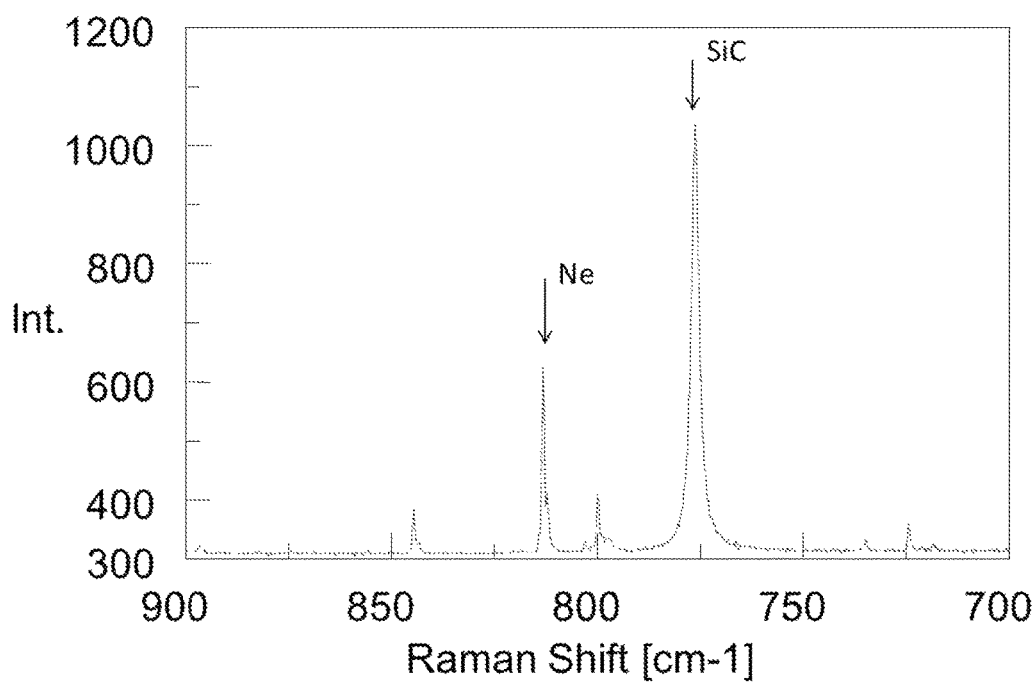
FIG. 4 is an example of Raman-scattered light measurement data on a bulk SiC single crystal.

In this case, for the measurement of the Raman shifts, a Raman spectrometer (NRS-7100 manufactured by JASCO Corporation, resolution: ±0.05 $cm^{-1}$) was used, and a 532 nm green laser was used as a light source. The light was applied so as to form a φ2 μm spot on the surface of each of the samples (reference SiC single crystal, and ingots A to D), and the depth of focus was adjusted to a depth of about 10 μm from the surface of each of the samples. Under those conditions, the measurement light was applied to a total of 72 spots, i.e., 8 rows×9 columns at a spot interval of 10 μm, and a Raman shift was determined from the average value of the 72 spots. In FIG. 4, an example of the measurement of Raman-scattered light (Raman shift spectrum of the ingot A) is shown, and a peak of the Ne lamp at 816 $cm^{-1}$ was used for the calibration of scattered light measurement. For the determination of the difference in Raman shift for one ingot, the measurement of the Raman shifts of the reference SiC single crystal and the ingot serving as an object to be evaluated took about 10 min in total.

TABLE 1

| SiC single crystal ingot | | | | Raman shift [$cm^{-1}$] | | Difference between Raman shifts (i) − (ii) |
|---|---|---|---|---|---|---|
| Name | Diameter | Height | Nitrogen concentration [atoms/$cm^3$] | (i) Ingot | (ii) Reference SiC | |
| A | 3 inches (Diameter: 80 mm) | 10 mm | $6.2 \times 10^{18}$ | First day of measurement 776.80 | 776.70 | 0.10 |

TABLE 1-continued

| | SiC single crystal ingot | | | Raman shift [cm⁻¹] | | Difference between Raman shifts |
|---|---|---|---|---|---|---|
| Name | Diameter | Height | Nitrogen concentration [atoms/cm³] | (i) Ingot | (ii) Reference SiC | (i) − (ii) |
| B | 4 inches (Diameter: 110 mm) | 10 mm | 4.1 × 10¹⁹ | Second day of measurement 776.81 | 776.65 | 0.16 |
| C | 5 inches (Diameter: 130 mm) | 15 mm | 9.0 × 10¹⁸ | Third day of measurement 776.70 | 776.50 | 0.20 |
| D | 5 inches (Diameter: 131 mm) | 14 mm | 2.5 × 10¹⁹ | Fourth day of measurement 776.56 | 776.35 | 0.21 |
| D' | 5 inches (Diameter: 131 mm) | " | " | Additional measurement (after annealing) 776.78 | 776.60 | 0.15 |

The differences in Raman shift were determined as described above for the ingots A to D, and the results revealed that, as shown in Table 1, the strain of the lattice increased in the order of A<B<C<D. In view of this, thin plate-like SiC single crystals each having a thickness of 0.5 mm were sequentially cut out of those respective four ingots with a multi-wire saw using loose abrasive grains. The ingot A and the ingot B were able to be cut without the generation of a crack, but in the cutting of the ingot C, a crack probably due to a strain was generated. The generation of a crack was similarly expected for the ingot D on the basis of its difference in Raman shift, and hence the ingot D was subjected to high-temperature annealing at a temperature of 2,200° C. for 28 hr. Then, for an ingot D after the high-temperature annealing treatment, in the same manner as above, the Raman shift $R_{ref}$ of the reference SiC single crystal was measured again, and the Raman shift $R_{D'}$ of the ingot D' was measured to determine a difference $(R_{D'}-R_{ref})$ between the Raman shifts. As a result, the resultant lattice strain was comparable to that of the ingot B. Accordingly, when a thin plate-like SiC single crystal was cut out using a multi-wire saw, cutting was actually able to be performed without the generation of a crack.

As just above, for an ingot having a large strain, the generation of a crack in a processing process can be prevented by, for example, performing annealing treatment in advance. In this case, an ingot having a small strain does not require annealing, and hence obviates the need for extra labor and cost.

Example 2

Figure 3B:
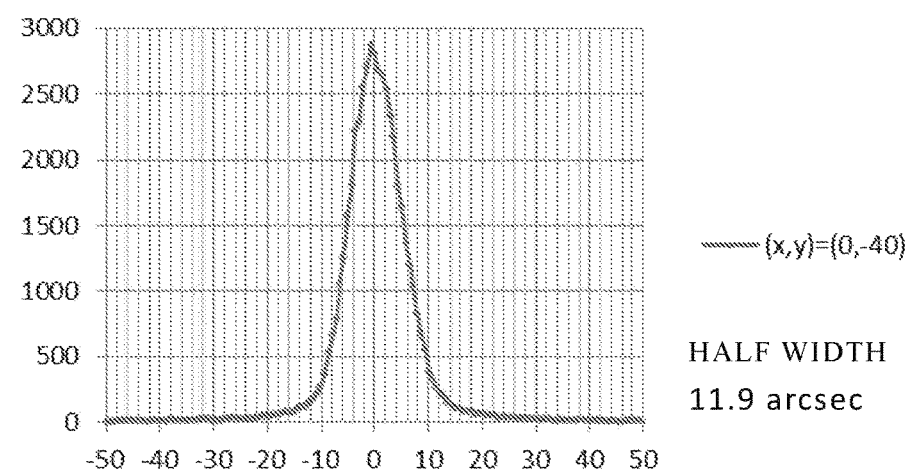
FIG. 3(b) is a graph for showing an X-ray rocking curve of a reference SiC single crystal used in Example 2.

A 4-inch (diameter: 105 mm) 4H-type SiC single crystal ingot produced by a sublimation recrystallization method was subjected to outer periphery grinding, and cut using a multi-wire saw into a thin plate shape having a thickness of 2 mm. After that, a square-shaped chip of 15 mm square was cut out of a substantially central portion of a radius connecting the center and circumference of the thin plate. In Example 2, a somewhat thick chip was made in consideration of handleability. Then, both of its Si surface and C surface were polished by diamond polishing to provide a reference SiC single crystal having a surface roughness Ra of 0.3 nm, a thickness of 1.9 mm, and a size of 15 mm×15 mm. The SiC single crystal ingot of which the reference SiC single crystal was taken out had a nitrogen concentration of 4.0×10¹⁹ atoms/cm³. Etch pits were observed through molten alkali etching in the vicinity of the reference SiC single crystal taken out, and the reference SiC single crystal was found to have a dislocation density of 3.7×10³/cm² and micropipes at 0.3/cm². Further, a wafer cut out of the SiC single crystal ingot of which the reference SiC single crystal was taken out was measured for its X-ray rocking curve and, as shown in FIG. 3(b), was found to have a half width of 11.9 arcsec.

In the same manner as in Example 1, the resultant reference SiC single crystal was subjected to X-ray diffraction (XRD) measurement to determine its lattice constants, which were as follows: c=10.05906, a=3.071485, m=2.659978. In addition, a Raman shift was measured for the reference SiC single crystal, and as a result, a peak wavenumber of 776.5 cm⁻¹ was obtained. However, the Raman shift changed depending on the measurement time slot and the measurement date, and varied approximately between 775.2 cm⁻¹ and 776.8 cm⁻¹.

Next, four kinds of SiC single crystal ingots E to H produced by a sublimation recrystallization method, each having a diameter of 4 inches, a nitrogen (N) doping concentration of from 5×10¹⁸ atoms/cm³ to 5×10¹⁹ atoms/cm³, and a polytype of 4H, were prepared. Those ingots were each subjected to outer periphery grinding processing, and then cut with a multi-wire saw to a thickness of 0.5 mm to produce 20 as-sliced substrates from each of the ingots. Then, one as-sliced substrate was taken from each of the ingots, and the substrates were each subjected to CMP polishing to prepare four kinds of SiC single crystal substrates e1 to h1 shown in Table 2 serving as objects to be evaluated.

Then, for each of the SiC single crystal substrates e1 to h1, a Raman shift was measured in the same manner as in Example 1. That is, on the first day of measurement, a Raman shift $R_{ref}$ was measured at the center of the reference SiC single crystal obtained as described above, and a Raman shift $R_{e1}$ was measured at the center in the Si surface of the SiC single crystal substrate e1 to determine a difference $(R_{e1}-R_{ref})$ between the Raman shifts. In addition, on the second day of measurement, the Raman shift $R_{ref}$ was measured again at the center of the reference SiC single crystal, and a Raman shift $R_{f1}$ was measured at the center in the Si surface of the SiC single crystal substrate f1 to determine a difference $(R_{f1}-R_{ref})$ between the Raman shifts. In this way, Raman shifts were similarly measured for the SiC single crystal substrate g1 (third day of measurement) and the SiC single crystal substrate h1 (fourth day of measurement) to determine differences between their Raman shifts and the Raman shift $R_{ref}$ of the reference SiC single crystal. The measurement took about 10 min in total for one SiC single crystal substrate, which was substantially the same as in Example 1.

TABLE 2

| Name | SiC single crystal substrate | | | Raman shift [cm$^{-1}$] | | Difference between Raman shifts (i) − (ii) |
| --- | --- | --- | --- | --- | --- | --- |
| | Diameter | Thickness | Nitrogen concentration [atoms/cm$^3$] | (i) Substrate | (ii) Reference SiC | |
| e1 | 4 inches (Diameter: 108 mm) | 0.35 mm | 6.5 × 10$^{18}$ | First day of measurement 776.95 | 776.90 | 0.05 |
| f1 | 4 inches (Diameter: 108 mm) | 0.35 mm | 3.0 × 10$^{19}$ | Second day of measurement 776.73 | 776.63 | 0.10 |
| g1 | 4 inches (Diameter: 109 mm) | 0.35 mm | 4.5 × 10$^{19}$ | Third day of measurement 776.88 | 776.73 | 0.15 |
| h1 | 4 inches (Diameter: 110 mm) | 0.35 mm | 9.7 × 10$^{18}$ | Fourth day of measurement 776.51 | 776.31 | 0.20 |

The differences in Raman shift were determined as described above, and as shown in Table 2, the results revealed that the strain of the lattice in the SiC single crystal substrate increased in the order of e1<f1<g1<h1. In view of this, for each of those four SiC single crystal substrates, a SiC single crystal having a film thickness of 30 μm was epitaxially grown by a CVD method, and the amounts of warpage before and after the epitaxial growth were compared. The results are shown in Table 3. Herein, the warpage amount is a value measured using a measuring instrument configured to optically determine planarity (flatness) from interference fringes (FlatMasterFM200 manufactured by Corning Tropel Corporation). In addition, the nitrogen (N) doping concentration in the epitaxial film in each case was set to 1.0×10$^{15}$ cm$^{-2}$.

TABLE 3

| Substrate | Epi film thickness [μm] | Warpage amount [μm] | | |
| --- | --- | --- | --- | --- |
| | | Before epi-growth | After epi-growth | Change amount |
| e1 | 30 | 10 | 15 | 5 |
| f1 | 30 | 20 | 30 | 10 |
| g1 | 30 | 20 | 35 | 15 |
| h1 | 30 | 27 | 47 | 20 |

As apparent from the results shown in Table 3, the change amount of warpage after the epitaxial growth increases in the order of increasing difference in Raman shift of the SiC single crystal substrate. That is, the strain of the lattice also means the magnitude of the inter-lattice distance of the SiC single crystal, and it is considered that a bimetallic effect based on a difference in inter-lattice distance between the epitaxial film having a low nitrogen doping concentration and the SiC single crystal substrate having a high nitrogen doping concentration represents warpage after the epitaxial growth.

In addition, one as-sliced substrate prepared from each of the SiC single crystal ingots E to H in advance was further taken out, and the substrates were each subjected to CMP polishing to further prepare four kinds of SiC single crystal substrates e2 to h2 shown in Table 4. Then, for each of the SiC single crystal substrates e2 to h2, a Raman shift was measured in the same manner as above.

TABLE 4

| Name | SiC single crystal substrate | | | Raman shift [cm$^{-1}$] | | Difference between Raman shifts (i) − (ii) |
| --- | --- | --- | --- | --- | --- | --- |
| | Diameter | Thickness | Nitrogen concentration [atoms/cm$^3$] | (i) Substrate | (ii) Reference SiC | |
| e2 | 4 inches (Diameter: 108 mm) | 0.35 mm | 6.4 × 10$^{18}$ | Fifth day of measurement 776.61 | 776.55 | 0.06 |
| f2 | 4 inches (Diameter: 108 mm) | 0.35 mm | 3.3 × 10$^{19}$ | Sixth day of measurement 776.84 | 776.75 | 0.09 |
| g2 | 4 inches (Diameter: 109 mm) | 0.35 mm | 4.5 × 10$^{19}$ | Seventh day of measurement 776.55 | 776.41 | 0.14 |
| h2 | 4 inches (Diameter: 110 mm) | 0.35 mm | 9.4 × 10$^{18}$ | Eighth day of measurement 776.74 | 776.54 | 0.20 |

The results shown in Table 4 revealed that the strain of the lattice increased in the order of e2<f2<g2<h2. In view of this, in the growth of a SiC epitaxial film for each of those four SiC single crystal substrates e2 to h2 by the CVD method, the film thickness was set to 30 μm for each of the SiC single crystal substrates e2 and f2, and the film thickness was set to 10 μm for each of the SiC single crystal substrates g2 and h2 (each having a common nitrogen doping concentration of $1.0 \times 10^{15}$ cm$^{-2}$). Then, the amounts of warpage before and after the epitaxial growth were compared. The results are shown in Table 5.

TABLE 5

| Substrate | Epi film thickness [μm] | Warpage amount [μm] | | |
|---|---|---|---|---|
| | | Before epi-growth | After epi-growth | Change amount |
| e2 | 30 | 12 | 17 | 5 |
| f2 | 30 | 18 | 28 | 10 |
| g2 | 10 | 21 | 26 | 5 |
| h2 | 10 | 24 | 34 | 10 |

As shown in Table 5, the change amount of warpage in each of the SiC single crystal substrates g2 and h2 was able to be suppressed. In view of the results, for example, when the film thickness is set to 30 μm in the epitaxial growth of the SiC single crystal for each of the rest of the as-sliced substrates obtained from the SiC single crystal ingots E and F, and the film thickness is assigned to be 10 μm for each of the rest of the as-sliced substrates obtained from the SiC single crystal ingots G and H, an excessive increase in warpage can be prevented to increase total yield.

As apparent from Examples described above, according to the present invention, lattice strains can be relatively evaluated among a plurality of bulk SiC single crystals. Moreover, even when not all of the objects to be evaluated are measured at the same timing, in the same place, and with the same apparatus, such evaluation can be performed. Accordingly, for example, when a plurality of factories far away from each other are each provided with a common reference SiC single crystal, through in-situ measurement of the strains of SiC single crystal substrates, SiC single crystal ingots, and the like produced at the respective factories, the magnitudes of their strains can be relatively compared instantly. In addition, through use of the evaluation method of the present invention, the generation of a crack during processing of a bulk SiC single crystal can be prevented, and the generation of warpage during the growth of an epitaxial film can be prevented.

Incidentally, in order to precisely measure a Raman shift, the wavenumber of a neon lamp is generally used as a standard. Strictly speaking, however, the light-emitting spectrum of the neon lamp itself also has a slight fluctuation. Accordingly, through utilization of the present invention, it is also possible to incorporate the reference SiC single crystal into a measuring apparatus, use the reference SiC single crystal as a standard, and determine the Raman shift of a SiC single crystal for measurement with respect to the standard. That is, when the "Raman spectrometry apparatus having incorporated thereinto the reference SiC single crystal" is adopted, there is no need to incorporate a neon lamp into the apparatus, and thus a Raman spectrometry apparatus of a simple structure capable of performing measurement with higher accuracy without being affected by fluctuation in wavenumber of the neon lamp can be constructed.

The invention claimed is:

1. An evaluation method for bulk-shaped silicon carbide single crystals, comprising:
    measuring a Raman shift $R_{ref}$ of a reference silicon carbide single crystal to be used as a standard;
    measuring respective Raman shifts $R_n$ of a plurality of bulk-shaped silicon carbide single crystals serving as objects to be evaluated;
    determining differences between each of the Raman shifts $R_n$ and the Raman shift $R_{ref}$;
    relatively comparing the differences,
    evaluating the magnitudes of strains of lattices in the plurality of bulk-shaped silicon carbide single crystals serving as objects to be evaluated based upon the compared differences, and
    performing treatment for removing an internal stress in the plurality of bulk-shaped silicon carbide single crystals serving as objects to be evaluated that have larger differences between Raman shifts $R_n$ and Raman shift $R_{ref}$.

2. An evaluation method for bulk-shaped silicon carbide single crystals according to claim 1, wherein the reference silicon carbide single crystal has a thickness of 100 μm or more and 2,000 μm or less and a surface roughness Ra of 1 nm or less.

3. An evaluation method for bulk-shaped silicon carbide single crystals according to claim 2,
    wherein the reference silicon carbide single crystal and the silicon carbide single crystals serving as objects to be evaluated each have a polytype of 4H, and
    wherein the reference silicon carbide single crystal has a micropipe density of 1.0/cm$^2$ or less and a dislocation density of $5 \times 10^3$/cm$^2$ or less.

4. An evaluation method for bulk-shaped silicon carbide single crystals according to claim 2,
    wherein the reference silicon carbide single crystal and the silicon carbide single crystals serving as objects to be evaluated each have a polytype of 4H, and
    wherein the reference silicon carbide single crystal has a half width of an X-ray rocking curve of 15 arcsec or less.

5. An evaluation method for bulk-shaped silicon carbide single crystals according to claim 2,
    wherein the reference silicon carbide single crystal and the silicon carbide single crystals serving as objects to be evaluated each have a polytype of 4H, and
    wherein the reference silicon carbide single crystal has lattice constants falling within the following ranges,
    $10.05903 \leq c \leq 10.05916$ (Å)
    $3.071114 \leq a \leq 3.071497$ (Å)
    $2.659663 \leq m \leq 2.659994$ (Å)
    wherein c, a, and m are lattice constants.

6. An evaluation method for bulk-shaped silicon carbide single crystals according to claim 2, wherein the reference silicon carbide single crystal and the silicon carbide single crystals serving as objects to be evaluated each comprise a silicon carbide single crystal produced by a sublimation recrystallization method.

7. An evaluation method for bulk-shaped silicon carbide single crystals according to claim 2, wherein the bulk-shaped silicon carbide single crystals serving as objects to be evaluated each comprise a silicon carbide single crystal ingot or a silicon carbide single crystal substrate.

8. An evaluation method for bulk-shaped silicon carbide single crystals according to claim 1, wherein the reference silicon carbide single crystal and the silicon carbide single crystals serving as objects to be evaluated each have a polytype of 4H, and wherein the reference silicon carbide single crystal has a micropipe density of 1.0/cm$^2$ or less and a dislocation density of 5×10$^3$/cm$^2$ or less.

9. An evaluation method for bulk-shaped silicon carbide single crystals according to claim 8, wherein the reference silicon carbide single crystal and the silicon carbide single crystals serving as objects to be evaluated each have a polytype of 4H, and wherein the reference silicon carbide single crystal has lattice constants falling within the following ranges, 10.05903≤c≤10.05916 (Å)

3.071114≤a≤3.071497 (Å)

2.659663≤m≤2.659994 (Å)

wherein c, a, and m are lattice constants.

10. An evaluation method for bulk-shaped silicon carbide single crystals according to claim 8, wherein the reference silicon carbide single crystal and the silicon carbide single crystals serving as objects to be evaluated each comprise a silicon carbide single crystal produced by a sublimation recrystallization method.

11. An evaluation method for bulk-shaped silicon carbide single crystals according to claim 8, wherein the bulk-shaped silicon carbide single crystals serving as objects to be evaluated each comprise a silicon carbide single crystal ingot or a silicon carbide single crystal substrate.

12. An evaluation method for bulk-shaped silicon carbide single crystals according to claim 1, wherein the reference silicon carbide single crystal and the silicon carbide single crystals serving as objects to be evaluated each have a polytype of 4H, and wherein the reference silicon carbide single crystal has a half width of an X-ray rocking curve of 15 arcsec or less.

13. An evaluation method for bulk-shaped silicon carbide single crystals according to claim 12, wherein the reference silicon carbide single crystal and the silicon carbide single crystals serving as objects to be evaluated each have a polytype of 4H, and wherein the reference silicon carbide single crystal has lattice constants falling within the following ranges, 10.05903≤c≤10.05916 (Å)

3.071114≤a≤3.071497 (Å)

2.659663≤m≤2.659994 (Å)

wherein c, a, and m are lattice constants.

14. An evaluation method for bulk-shaped silicon carbide single crystals according to claim 12, wherein the reference silicon carbide single crystal and the silicon carbide single crystals serving as objects to be evaluated each comprise a silicon carbide single crystal produced by a sublimation recrystallization method.

15. An evaluation method for bulk-shaped silicon carbide single crystals according to claim 1, wherein the reference silicon carbide single crystal and the silicon carbide single crystals serving as objects to be evaluated each have a polytype of 4H, and wherein the reference silicon carbide single crystal has lattice constants falling within the following ranges, 10.05903≤c≤10.05916 (Å)

3.071114≤a≤3.071497 (Å)

2.659663≤m≤2.659994 (Å)

wherein c, a, and m are lattice constants.

16. An evaluation method for bulk-shaped silicon carbide single crystals according to claim 15, wherein the reference silicon carbide single crystal and the silicon carbide single crystals serving as objects to be evaluated each comprise a silicon carbide single crystal produced by a sublimation recrystallization method.

17. An evaluation method for bulk-shaped silicon carbide single crystals according to claim 1, further comprising:

producing the reference silicon carbide single crystal and the silicon carbide single crystals serving as objects to be evaluated by a sublimation recrystallization method.

18. An evaluation method for bulk-shaped silicon carbide single crystals according to claim 1, further comprising:

producing a silicon carbide single crystal ingot or a silicon carbide single crystal substrate as the bulk-shaped silicon carbide single crystals serving as objects to be evaluated.

19. An evaluation method for bulk-shaped silicon carbide single crystals according to claim 1, further comprising:

attaching the bulk-shaped silicon carbide single crystals serving as objects to be evaluated onto a supporting pedestal having a horizontal mounting surface before measuring the Raman shifts $R_n$ thereof when the bulk-shaped silicon carbide single crystals serving as objects to be evaluated have a thickness of 500 μm or less.

* * * * *